US011058787B2

(12) United States Patent
Gass

(10) Patent No.: US 11,058,787 B2
(45) Date of Patent: Jul. 13, 2021

(54) SCENTED FRAME CLIP

(71) Applicant: Pamela Gass, Orlando, FL (US)

(72) Inventor: Pamela Gass, Orlando, FL (US)

(*) Notice: Subject to any disclaimer, the term of this patent is extended or adjusted under 35 U.S.C. 154(b) by 429 days.

(21) Appl. No.: 16/163,631

(22) Filed: Oct. 18, 2018

(65) Prior Publication Data

US 2019/0111172 A1 Apr. 18, 2019

Related U.S. Application Data

(60) Provisional application No. 62/573,758, filed on Oct. 18, 2017.

(51) Int. Cl.
*A61L 9/12* (2006.01)
*A61L 9/04* (2006.01)
*F16B 2/20* (2006.01)
*F16B 2/06* (2006.01)

(52) U.S. Cl.
CPC .............. *A61L 9/12* (2013.01); *A61L 9/042* (2013.01); *F16B 2/06* (2013.01); *F16B 2/20* (2013.01); *A61L 2209/15* (2013.01)

(58) Field of Classification Search
CPC ........ A61L 9/12; A61L 9/042; A61L 2209/15; F16B 2/06; F16B 2/20
See application file for complete search history.

(56) References Cited

U.S. PATENT DOCUMENTS

| 4,523,870 A | * | 6/1985 | Spector | ..................... A61L 9/12 239/55 |
| 5,735,460 A | * | 4/1998 | Eisenbraun | ............... A61L 9/03 239/34 |
| 2003/0079319 A1 | * | 5/2003 | McAllister | ................ B65F 1/06 24/536 |
| 2013/0062489 A1 | * | 3/2013 | DiNello | .................... A47G 1/06 248/224.8 |

FOREIGN PATENT DOCUMENTS

DE 19637034 A1 * 3/1998

OTHER PUBLICATIONS

Derwent Abstract of DE19637034 A1, published Mar. 1998 (Year: 1998).*

* cited by examiner

*Primary Examiner* — Sean E Conley
(74) *Attorney, Agent, or Firm* — Kelly G. Swartz; Widerman Malek, PL

(57) ABSTRACT

An ornamental including first and second elongate members, a transverse member, and a reservoir. The first elongate member having an inner side and an opposing outer side. The second elongate member having an outer side and an opposing inner side facing the inner side of the first elongate member. The transverse member having a first end connected directly to a first end of the first elongate member and a second end connected directly to a first end of the second elongate member. The reservoir affixed to the second end of the first elongate member.

19 Claims, 10 Drawing Sheets

SCENTED FRAME CLIP

RELATED APPLICATIONS

This application claims the benefit under 35 U.S.C. § 119(e) of U.S. Provisional Patent Application Ser. No. 62/573,758 filed on Oct. 18, 2017 and titled Ornamental Scented Frame Clip, the entire content(s) of which is/are incorporated herein by reference.

FIELD OF THE INVENTION

The present invention relates to systems for securing fragrance emitting devices to picture frames. More specifically, the present invention is directed to a device adapted to secure to a picture frame, carry a fragrance, and provide ornamentation.

BACKGROUND OF THE INVENTION

Existing fragrance products are not customizable. Additionally, existing fragrance products are not adapted to secure to picture frames or other ornamentation commonly found in a home. There exists a need for a product that is customizable and can be used in combination with existing household ornamentation.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

With the above in mind, embodiments of the present invention are related to an ornamental clip including first and second elongate members, a transverse member, and a reservoir. The first elongate member may have an inner side and an opposing outer side. The second elongate member may have an outer side and an opposing inner side facing the inner side of the first elongate member. The transverse member may have a first end connected directly to a first end of the first elongate member and a second end connected directly to a first end of the second elongate member. The reservoir may be affixed to the second end of the first elongate member.

The first elongate member, the second elongate member, and the transverse member may be cooperatively sized and positioned to form an interference fit with a picture frame positioned between the first and second elongate members.

The ornamental clip may further include a first and second grip. The first grip may be located on the inner side of the first elongate member. The second grip may be located on the inner side of the second elongate member and opposing the first grip. The first and second grip may be configured to increase the coefficient of friction between the first or second elongate member and an item secured therebetween.

The second elongate member may further include a first angled portion, a straight portion, and a second angled portion. The first angled portion may be connected directly to the transverse member at a first end of the first angled portion. The first angled portion may extend downwardly from the transverse member and form an acute angle between the transverse member and the inner side of the second elongate member. The straight portion may have a first end connected directly to a second end of the first angled portion, which may oppose the first end of the first angled portion. The straight portion may form a reflex angle between the first angled portion and the inner side of the straight portion. The second angled portion may have a first end connected directly to a second end of the straight portion, which may oppose the first end of the straight portion. The second angled portion may form a reflex angle between the second angled portion and the inner side of the straight portion.

The ornamental clip may further include a grip located on the straight portion of the second elongate member and configured to increase the coefficient of friction between the second elongate member and an item secured between the first and second elongate members.

The ornamental clip may include a scented substance carried by the reservoir.

The ornamental clip may include ornamentation removably secured to the outer side of the first elongate member.

The ornamentation may be adapted to carry a material having a thickness and a decoration disposed thereon. The ornamentation may include a first and second opening. The first opening may be adapted to receive the material and have a length greater than a width of the material. The second opening may be adapted to have a perimeter smaller than a perimeter of the material and be adapted to display the decoration therethrough.

The ornamental clip may further include first and second connectors. The first connector may be secured to the outer side of the first elongate member. The second connector may be secured to an inner side of the ornamentation. The first and second connectors may be cooperatively configured to secure to one another.

The first elongate member may further include a first straight portion, a first angled portion, a second straight portion, and a second angled portion. The first straight portion may have a first end and a second end, which opposes the first end. The first end of the first straight portion may connect directly to the first end of the transverse member. The first straight portion may extend downwardly from the transverse member and form a right angle between the transverse member and the inner side of the first straight portion. The first angled portion may have a first end and a second end, which opposes the first end. The first end of the first angled portion may connect directly to the second end of the first straight portion. The first angled portion may form an obtuse angle between the first straight portion and the inner side of the first angled portion. The second straight portion may have a first end and a second end, which opposes the first end. The first end of the second straight portion may connect directly to the second end of the first angled portion. The second straight portion may form a reflex angle between the first angled portion and the inner side of the second straight portion. The second angled portion may have a first end and a second end, which opposes the first end. The first end of the second angled portion connects directly to the second end of the second straight portion. The second angled portion may form a reflex angle between the second straight portion and the inner side of the second angled portion.

The ornamental clip may further include a grip located on the second straight portion of the first elongate member and configured to increase the coefficient of friction between the first elongate member and an item secured between the first and second elongate members.

The reservoir may connect directly to the second end of the second angled portion.

The ornamental clip may further include ornamentation removably secured to the outer side of the first straight portion of the first elongate member.

The first connector may include a mounting portion and the second connector may include an opening adapted to receive and carry the mounting portion with an interference fit.

The reservoir may include a base, a front side, a back side, a first side, and a second side. The base may have a first side edge, a second side edge, which opposes the first side edge, a front edge, and a back edge. The front side may be secured to the front edge and extend upwardly from the base. The back side may be secured to the back edge and extend upwardly from the base. The first side may be secured to the first side edge, the front side, and the back side and extend upwardly from the base. The second side may be secured to the second side edge, the front side, and the back side and may extend upwardly from the base. The base, front side, back side, first side, and second side may define a cavity.

The first side may include a plurality of openings through an entirety of a thickness of the first side. The second side may include a plurality of openings through an entirety of a thickness of the second side.

The ornamental clip may further include a cover carried by the reservoir and cooperatively formed with the reservoir to enclose the cavity.

DETAILED DESCRIPTION OF THE INVENTION

Figure 1:
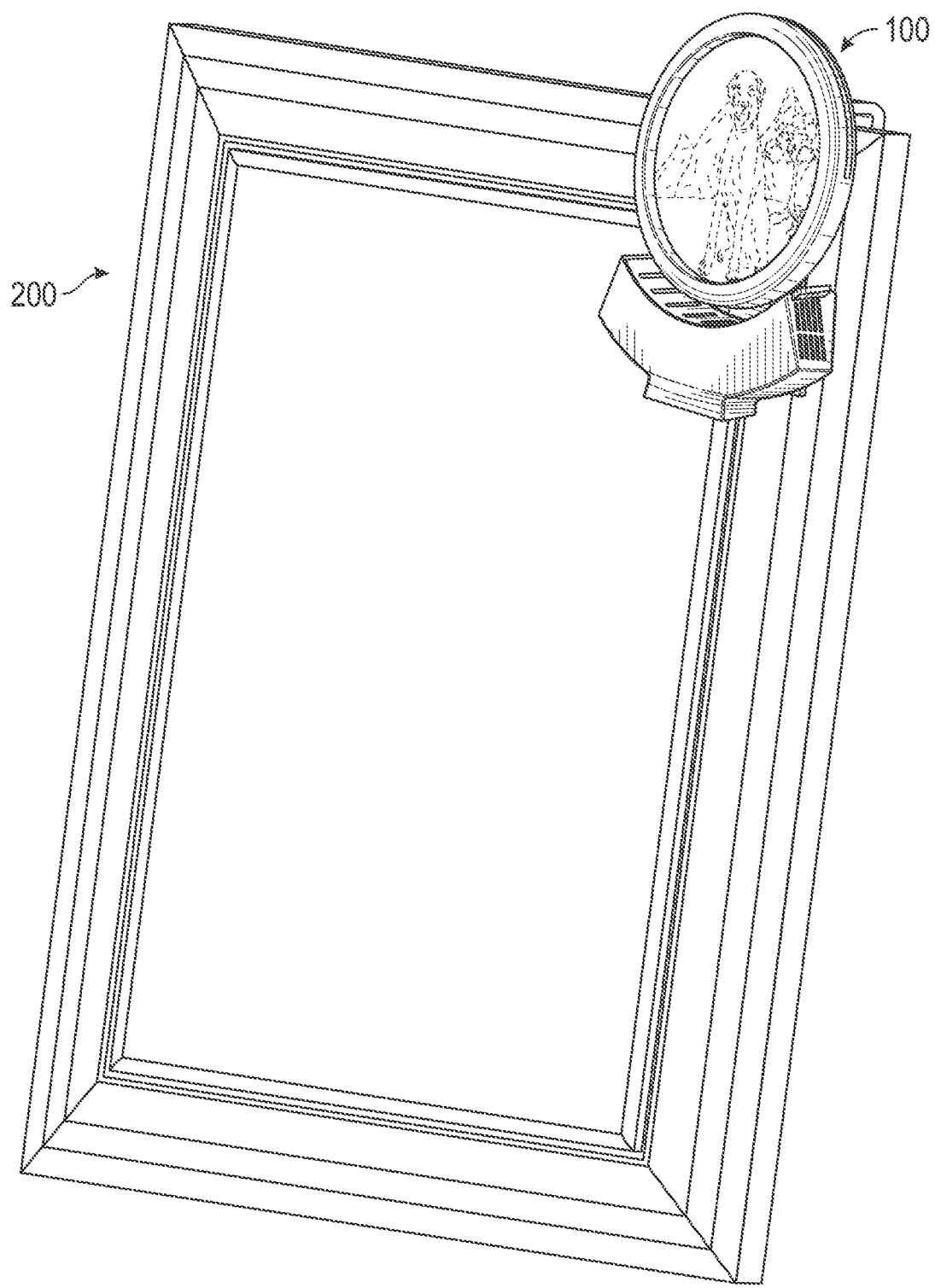
FIG. 1 is an environmental view of an ornamental scented frame clip secured to a picture frame according to an embodiment of the present invention.
Figure 2:
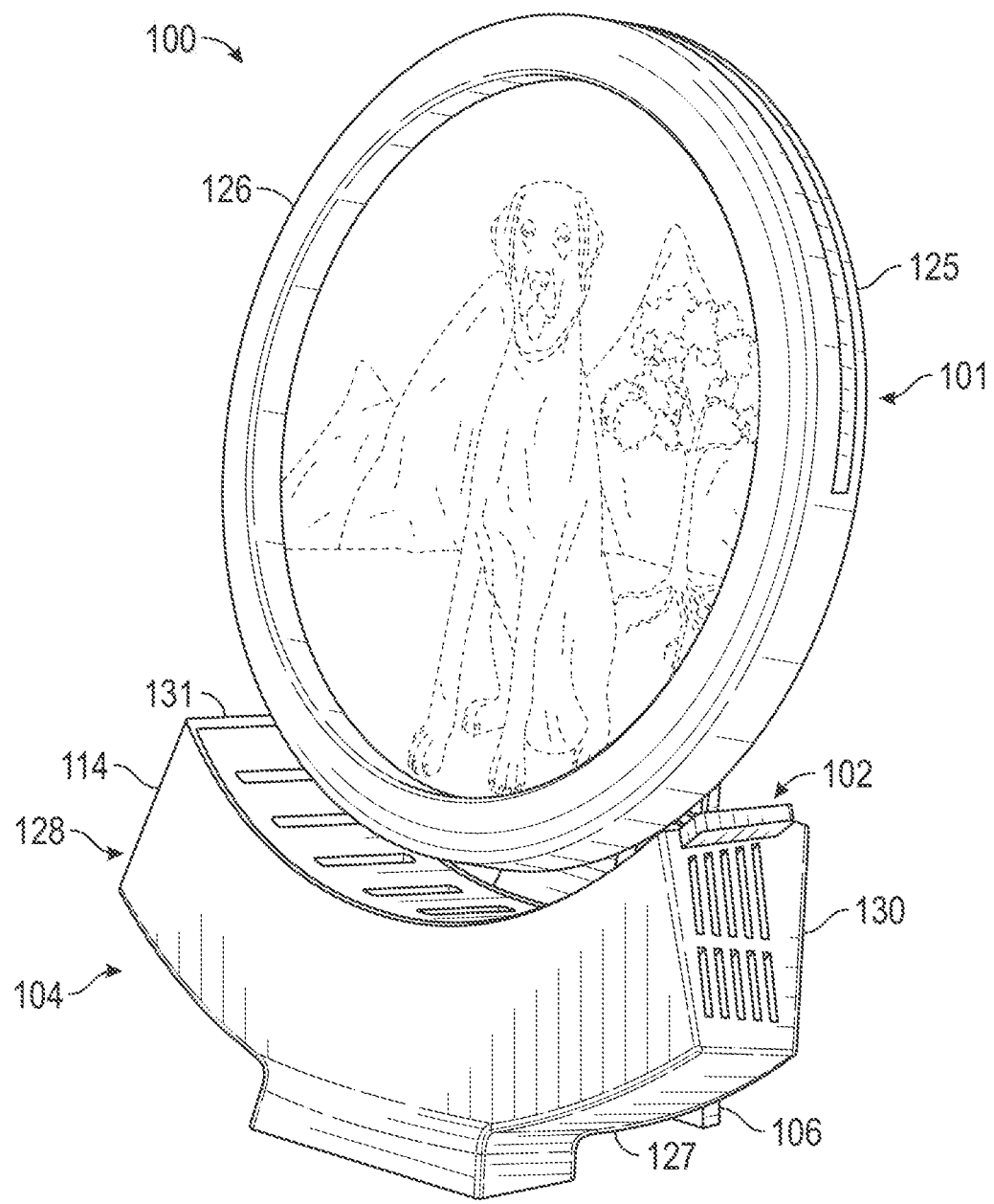
FIG. 2 is a front perspective view of the ornamental scented frame clip of FIG. 1.
Figure 3:
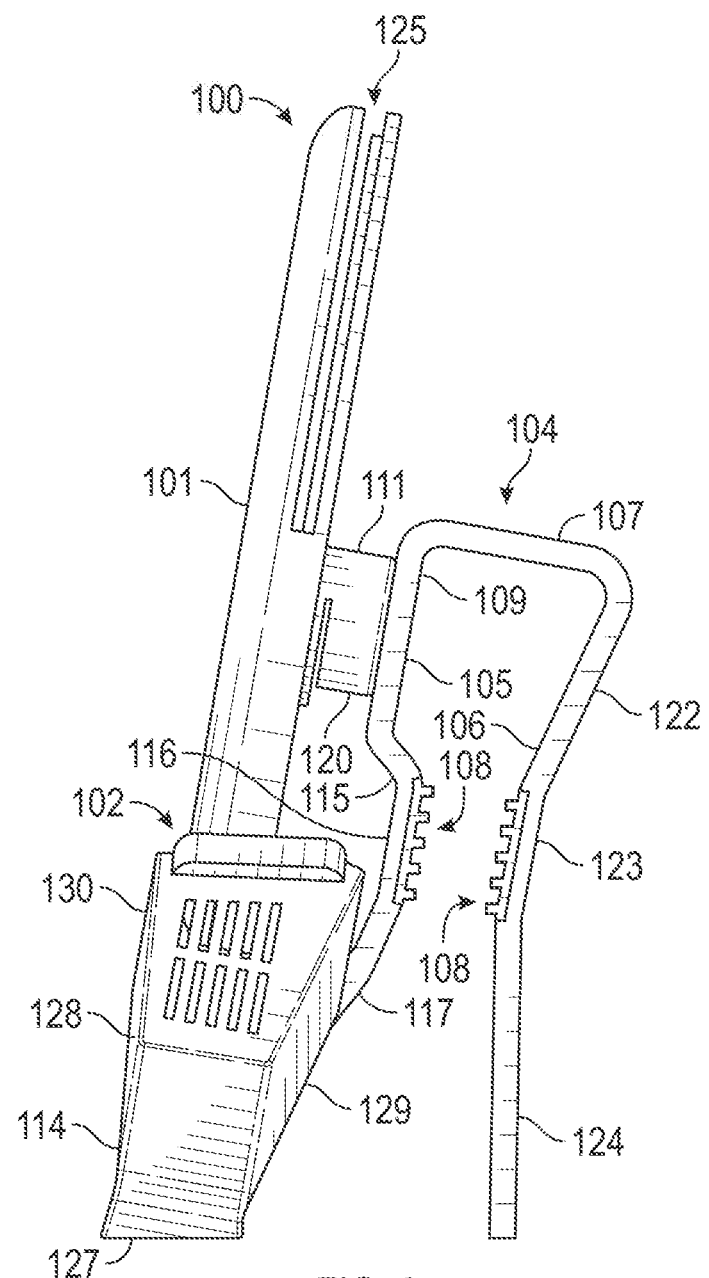
FIG. 3 is a side elevation view of the ornamental scented frame clip of FIG. 1.
Figure 4:
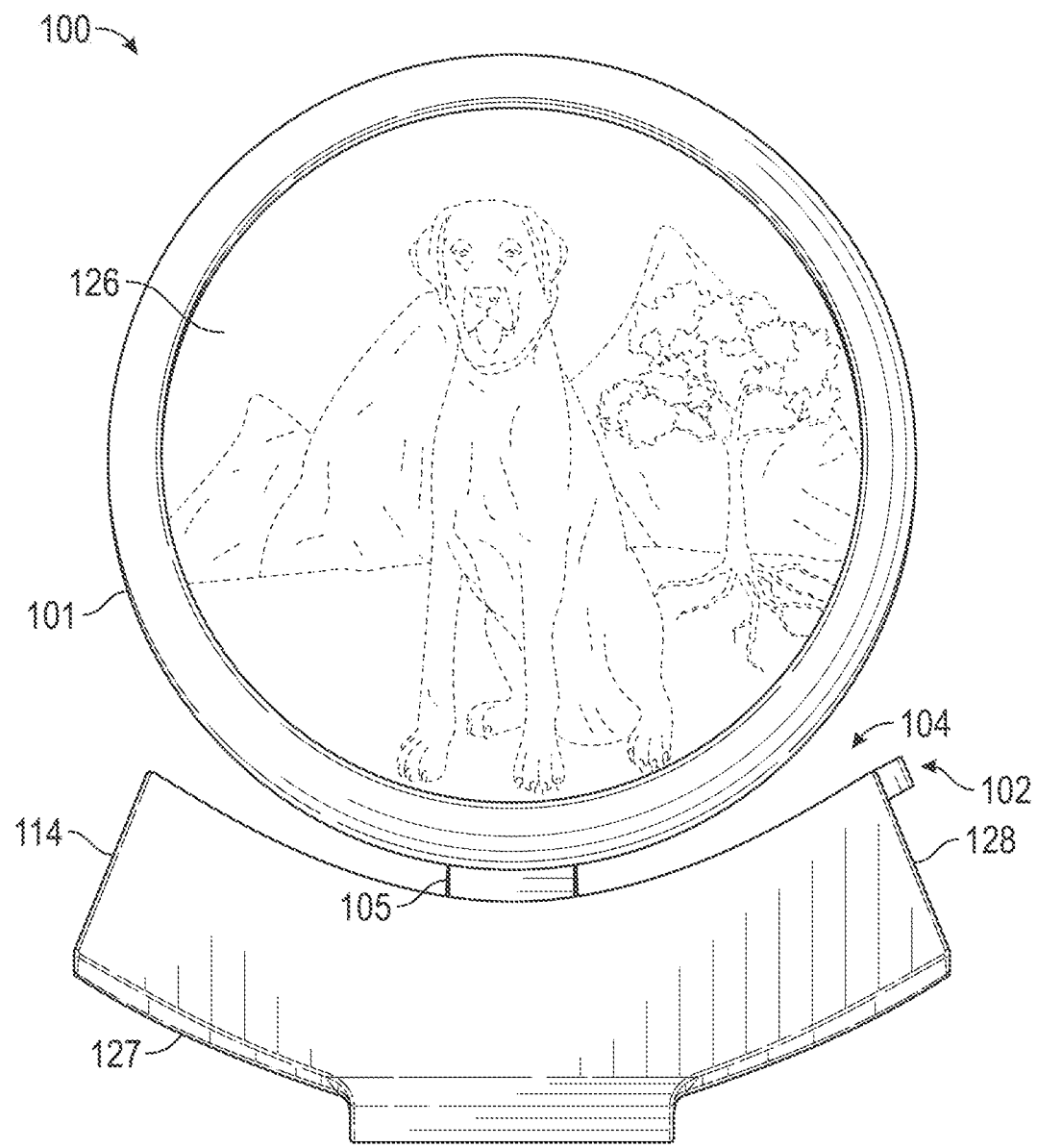
FIG. 4 is a front elevation view of the ornamental scented frame clip of FIG. 1.
Figure 5:
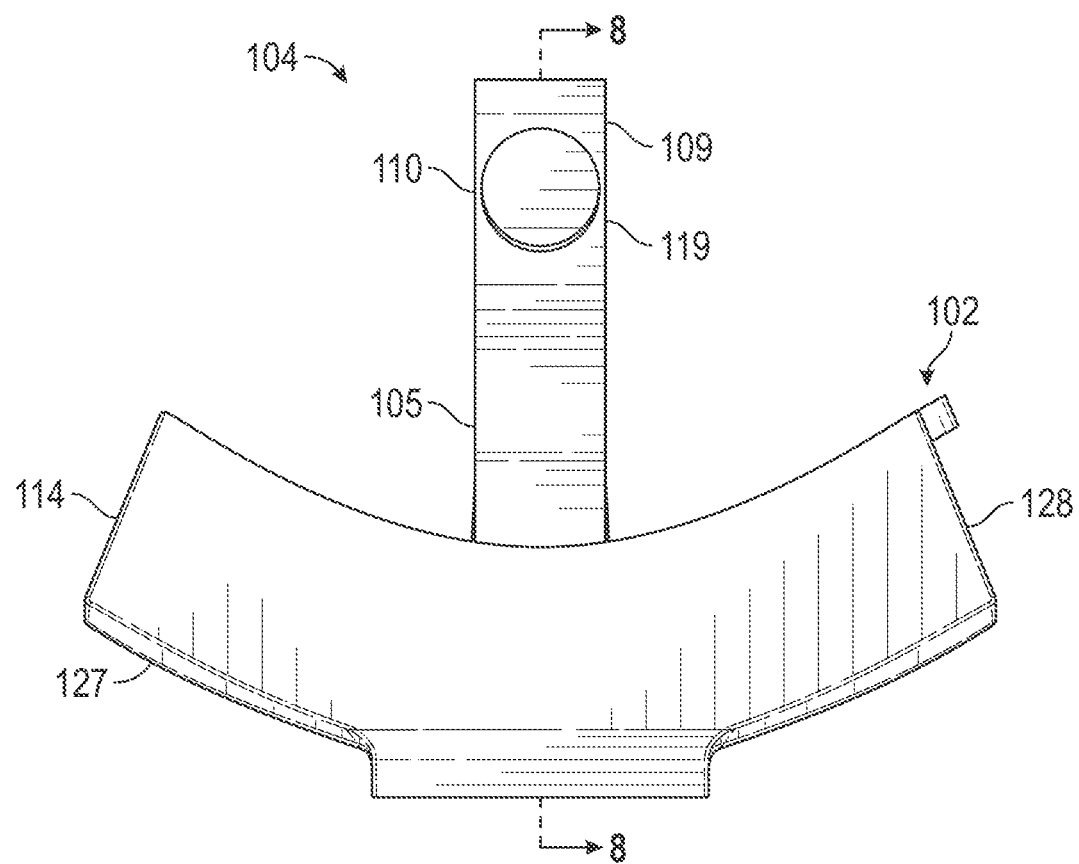
FIG. 5 is a front elevation view of the clip portion of the ornamental scented frame clip of FIG. 1.
Figure 6:
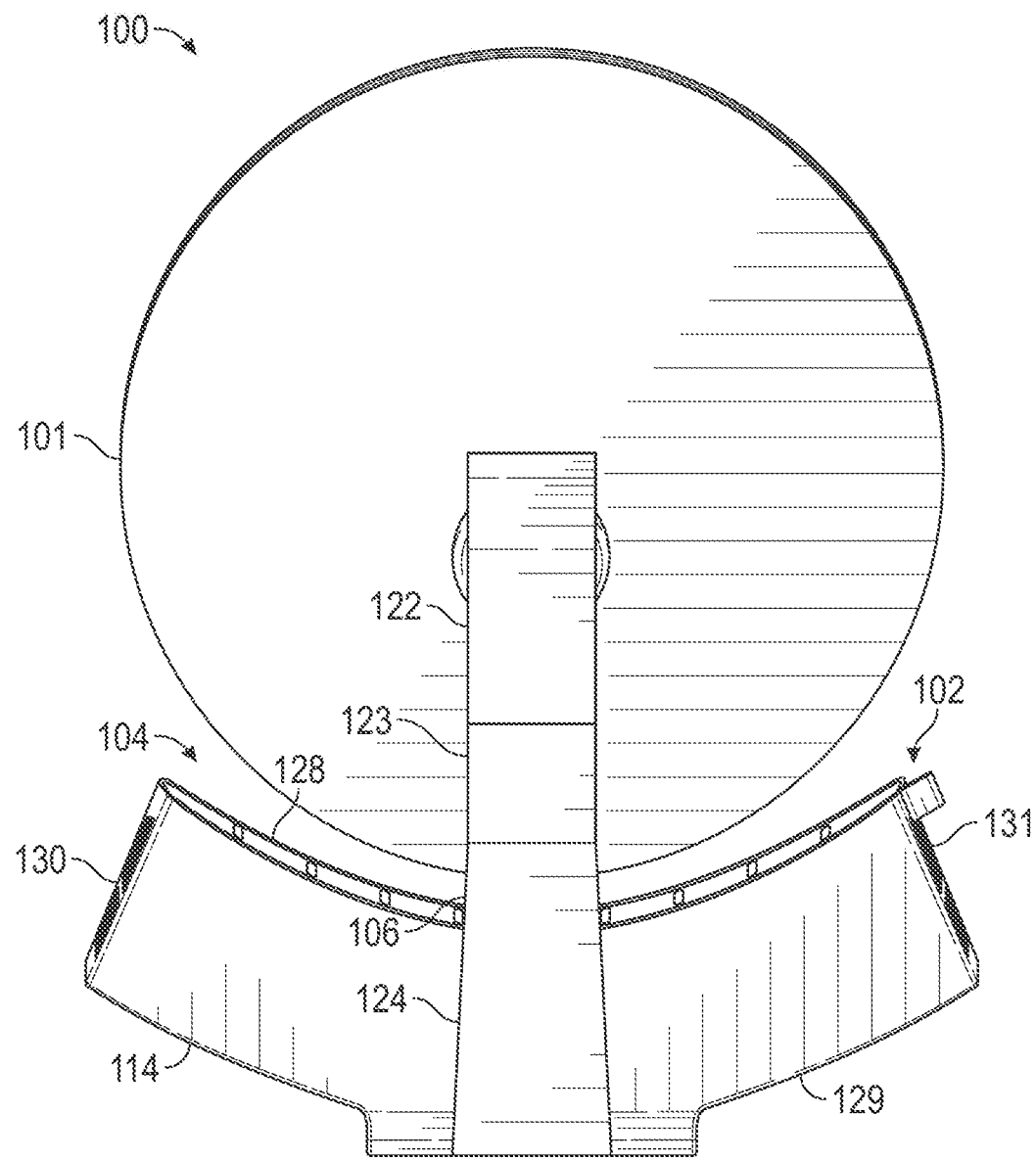
FIG. 6 is a rear elevation view of the ornamental scented frame clip of FIG. 1.
Figure 7:
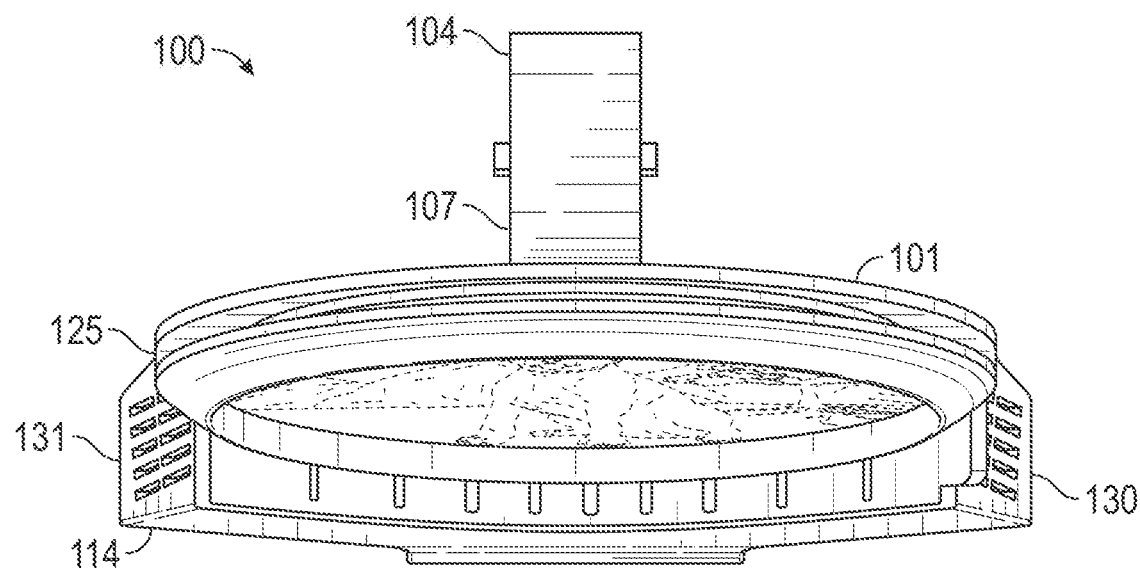
FIG. 7 is a top plan view of the ornamental scented frame clip of FIG. 1.
Figure 8:
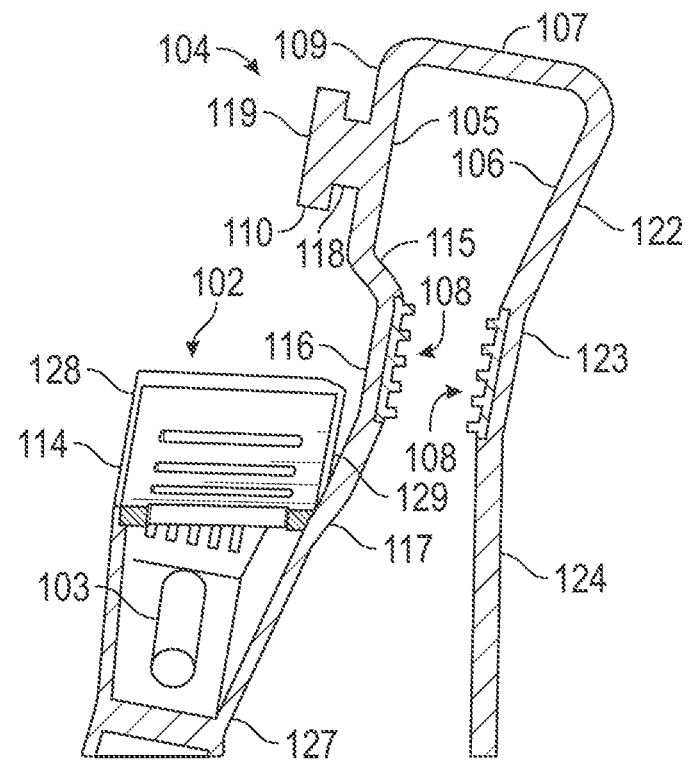
FIG. 8 is a cross-section view of the clip portion taken through the line 8-8 in FIG. 5.
Figure 9:
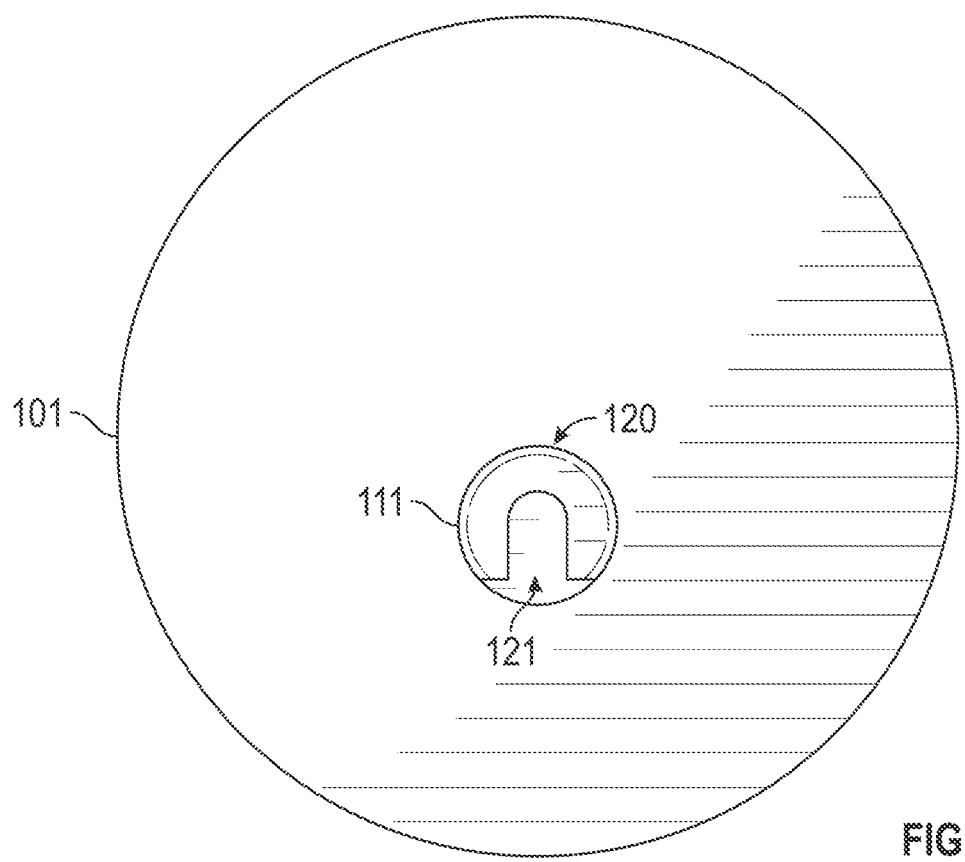
FIG. 9 is a rear elevation view of the removable ornamentation of the ornamental scented frame clip of FIG. 1.
Figure 10:
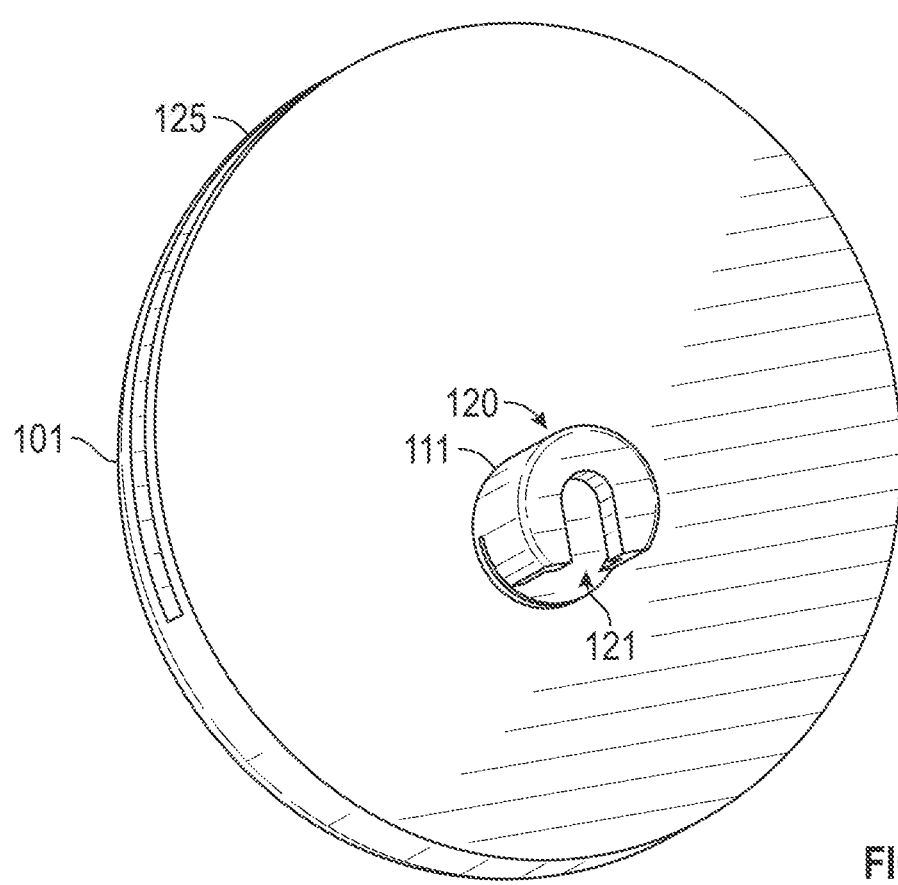
FIG. 10 is a bottom perspective view of the removable ornamentation of FIG. 9.
Figure 11:
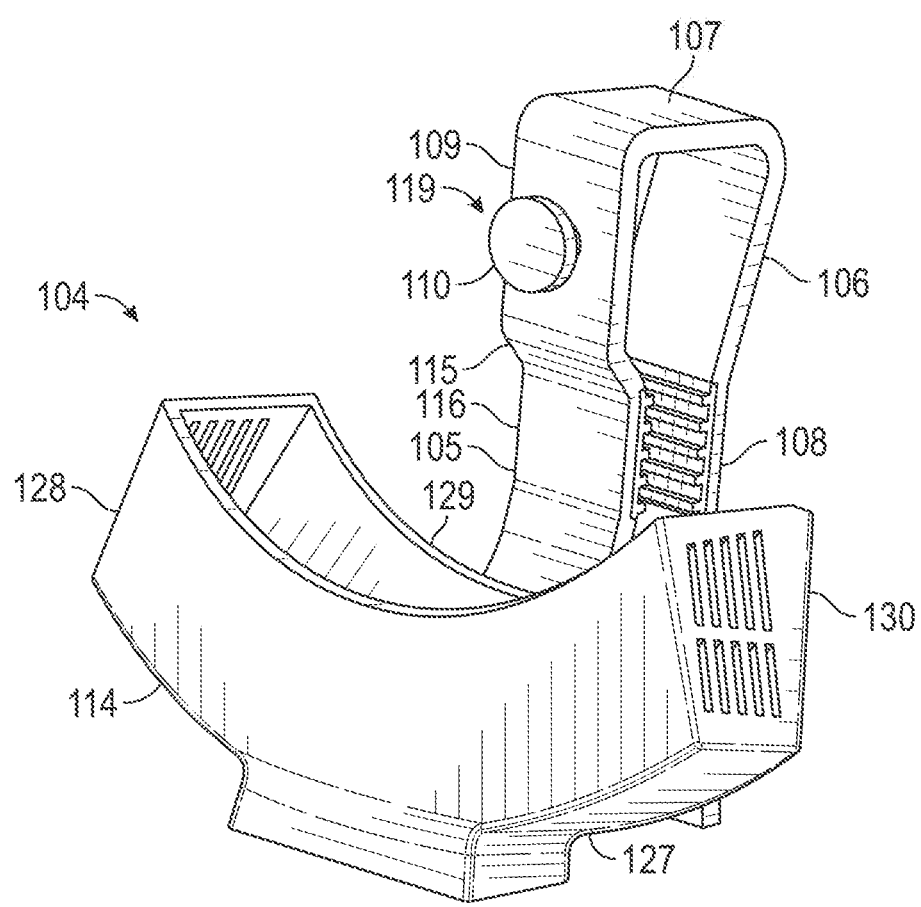
FIG. 11 is a side perspective view of the clip portion of FIG. 5 with the scent strip cover removed.
Figure 12:
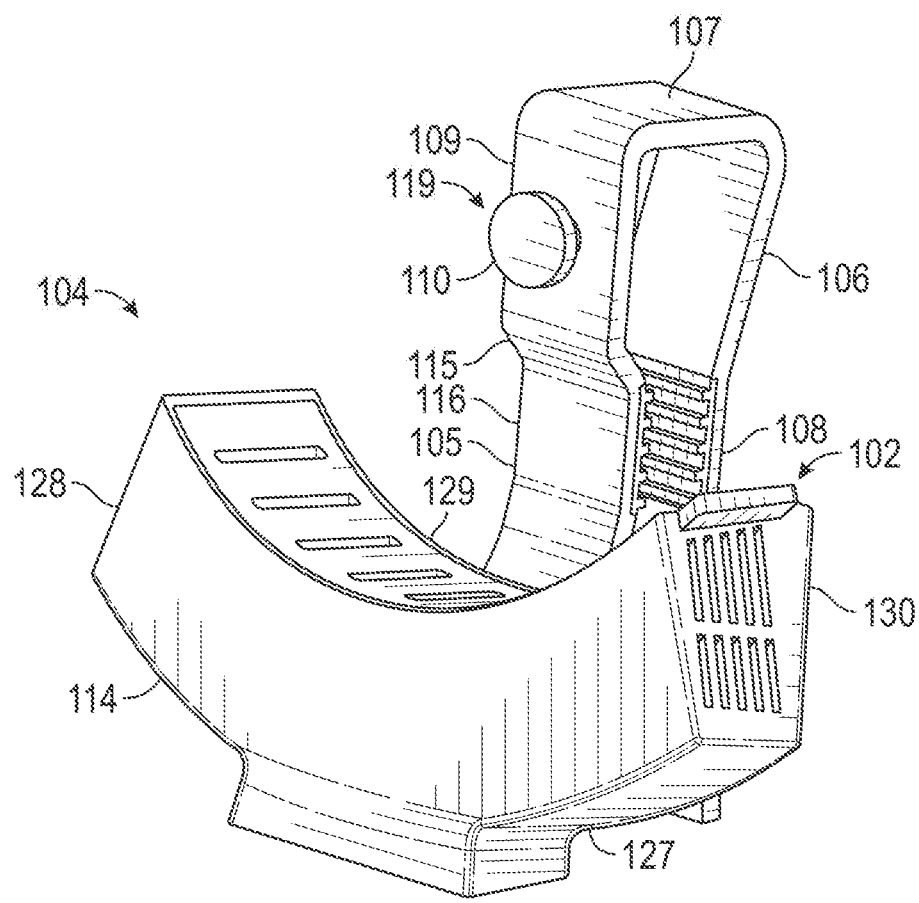
FIG. 12 is a side perspective view of the clip portion of FIG. 5.
Figure 13:
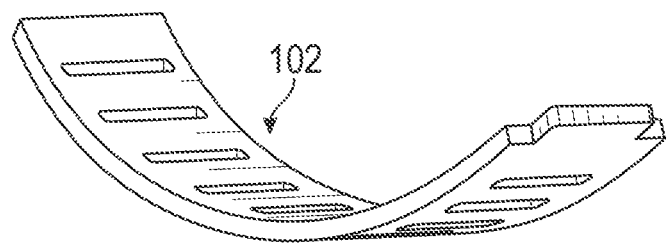
FIG. 13 is a side perspective view of the scent strip cover of the ornamental scented frame clip of FIG. 1.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

An embodiment of the invention, as shown and described by the various figures and accompanying text, provides an ornamental scented frame clip 100. The ornamental scented frame clip may include a clip portion 104, a removable ornamentation 101, a scent strip reservoir 114, and a scent strip cover 102.

The clip portion 104 may be adapted to secure to a picture frame 200. The clip portion 104 may have a first elongate member 105 opposing a second elongate member 106. The first elongate member 105 may be secured to the second elongate member 106 by a transverse member 107. The transverse member 107 may extend between and join a first end of the first elongate member 105 to a first end of the second elongate member 106. Both the first elongate member 105 and the second elongate member 106 may extend away from the transverse member 107 in a downward direction. The first elongate member 105 and the second elongate member 106 may not both lie in the same plane, but they may both be in different planes than the transverse member 107.

The first elongate member 105 and the second elongate member 106 may be cooperatively adapted to secure to a picture frame 200 positioned between the two elongate members 105, 106. The transverse member 107 may be configured to position the first elongate member 105 a sufficient distance from the second elongate member 106 to allow a picture frame 200 to be secured between the two elongate members 105, 106. Each elongate member 105, 106 may have an inner side positioned to face the inner side of the opposing elongate member 105, 106. At least a portion of each inner side may be adapted to contact a surface of the picture frame 200 and secure the ornamental scented frame clip 100 to the picture frame 200 with an interference fit. In one embodiment, a gripping surface 108 may be located on at least a portion of the inner side of the first elongate member or the second elongate member 106. The gripping surface 108 may be adapted to increase friction with the surface it contacts when compared to the surrounding inner side of the elongate members 105, 106. In one embodiment, the gripping surface 108 may include a rubberized material with a plurality of raised ridges. A gripping surface 108 on the inner side of the first elongate member 105 may directly oppose a gripping surface 108 on the inner side of the second elongate member 106. The first and second elongate members 105, 106 may be contoured so that only the gripping surfaces 108 contact the frame 200 when the ornamental scented frame clip 100 is secured thereto.

The first elongate member 105 may have a second end opposing the first end. The second end may be secured to a scent strip reservoir 114. The second end of the first elongate member 105 may bow outward away from the second elongate member 106. The first elongate member 105 may have a center portion adapted to bow inwards toward the second elongate member 106. The portion of the inner side of the first elongate member 105 closest to the second elongate member 106 may be covered by a gripping surface 108. A first straight portion 109 of the first elongate member 105 located near the first end may extend essentially perpendicularly downwardly from the transverse member 107. The first straight portion 109 may have an outer side opposing the inner side. A first connector 110 may be positioned on the outer side of the first straight portion 109 or on any portion of the outer side of the first elongate member 105. The first connector 110 may be adapted to secure removable ornamentation 101 to the ornamental scented frame clip 100.

The first elongate member 105 may include a first straight portion 109. The first straight portion 109 may have a first and an opposing second end. The first end of the first straight portion 109 may secure directly to the first end of the transverse member 107 and extend downwardly essentially perpendicular to the transverse member 107. The first elongate member 105 may also include a first angled portion 115 having a first and an opposing second end. The first end of the first angled portion 115 may secure directly to the second end of the first straight portion 109. The first angled portion 115 may form an obtuse angle with the inner side of the first straight portion 109. The first elongate member 105 may further still include a second straight portion 116 having a first end and an opposing second end. The first end of the second straight portion 116 may secure directly to the second end of the first angled portion 115. The second straight portion 116 may form a reflex angle with the inner side of the first angled portion 115. A gripping surface 108 may be secured directly to the inner side of the second straight portion 116. The second straight portion 116 and the first straight portion 109 may be essentially parallel. The sum of the reflex angle formed between the second straight portion 116 and the first angled portion 115 plus the obtuse angle formed between the first angled portion 115 and the first straight portion 109 may equal 360 degrees. The second end of the second straight portion 116 may secure directly to a first end of the second angled portion 117. The second straight portion 116 and the inner side of the second angled portion 117 may form a reflex angle.

In one embodiment, the first connector 110 may include a stem 118 with a first end secured directly to the outer side and extending away from the first elongate member 105 perpendicularly. The second end of the stem may oppose the first end and be fixedly secured to a mounting portion 119. The mounting portion 119 may have a circumference or outer diameter greater than the circumference or outer diameter of the stem 118. The first connector 110 may be adapted to mate to a second connector 111 located on the removable ornamentation 101 and thereby carry the removable ornamentation 101.

The second connector 111 may be adapted to receive the mounting portion 119 of the first connector 110. The second connector 111 may have a housing 120 including an outer wall with a first edge fixed to and extending perpendicularly away from the back side of the removable ornamentation 101. The outer wall may have a perimeter shaped as a portion of the perimeter of the mounting portion 119. The outer wall may not entirely enclose an inner area defined by the outer wall. A void may be left in the outer wall, which void may be adapted to receive the stem 118 of the first connector 110. The second edge of the outer wall may oppose the first edge and secure to a retaining edge. The retaining edge may be perpendicular to the outer wall and in a plane parallel to the plane of the back side of the removable ornamentation 101. The retaining edge may secure to the outer wall along an entirety of the second edge of the outer wall and extend toward the center of the removable ornamentation 101. The retaining wall may have a void in the middle portion of the wall. The circumference or perimeter of the void may be larger than the circumference or perimeter of the stem 118 of the first connector 110. The height of the outer wall may be greater than the thickness of the mounting portion 119 of the first connector 110. The outer wall and retaining wall may be cooperatively adapted to carry the mounting portion within the walls with the stem extending through the void in the retaining wall. The walls may be sufficiently flexible to allow the removable ornamentation 101 to be secured to and removed from the first connector 110. End portions of the outer wall may not be secured to the back side of the ornamental portion at the first edge. Such a configuration may allow the outer walls flexibility to mate and de-mate with the first connector 110.

The second connector 111 may include a housing 120 adapted to receive the mounting portion 119. The housing 120 may have an interior circumference slightly larger than the circumference of the mounting portion 119 and may be adapted to receive the mounting portion 119 within an interior void defined by the housing 120. The housing 120 may have a slot 121 adapted to receive the stem 118 when the mounting portion 119 is carded within the void defined by the housing 120. The height of the housing 120 may be defined as the distance from the back surface of the removable ornamentation 101 to the inner surface of the wall of the housing 120 surrounding the slot 121. The height of the housing 120 may be slightly larger than the thickness of the mounting portion 119. The housing 120 and slot 121 may be cooperatively configured to carry the mounting portion 119 and stem 118 with an interference fit.

The second elongate member 106 may have a second end opposing the first end. While the first end may be secured to the transverse member 107, the second end may not be secured to another structure and may remain free. The second elongate member 106 may have a center portion adapted to bow inwards toward the first elongate member 105. The portion of the inner side of the second elongate member 106 closest to the first elongate member 105 may be covered by a gripping surface 108. The second end of the second elongate member 106 may be configured to allow a user to grasp the second end and exert pressure to move the first elongate member 105 away from the second elongate member 106, thereby removing friction placed on the picture frame 200 and allowing the picture frame 200 to be removed from between the two elongate members 105, 106.

The second elongate member 106 may include a first angled portion 122 having a first end connected directly to the transverse member 107. The first angled portion 122 may extend downwardly from the transverse member 107 and inwardly toward the first elongate member 105, forming an acute angle between the bottom side of the transverse member 107 and the inner side of the first angled portion 122. A straight portion 123 may have a first end secured directly to the second end of the first angled portion 122. An inner side of the straight portion 123 may form a reflex angle with the inner side of the first angled portion 122. The straight portion 123 may be essentially parallel to the first straight portion 109 and second straight portion 116 of the first elongate member 105. The straight portion 123 may form essentially a right angle with the transverse member 107. The inner side of the straight portion 123 may be secured directly to a gripping surface 108. A second end of the straight portion 123 may secure directly to a first end of the second angled portion 124. An inner side of the second angled portion 124 may form a reflex angle with the inner side of the straight portion 123.

Removable ornamentation 101 may be secured to and removed from the clip portion 104 by mating and de-mating the first connector 110 and second connector 111. The second connector 111 may be fixedly secured to the back side of the removable ornamentation 101. The removable ornamentation 101 may include a frame, which is adapted to carry a material, which may include a photo or other decoration disposed on the material. The material may have a thickness, which is received by a first opening 125 of the frame on the body of the removable ornamentation 101. The first opening 125 may extend along one edge of the frame in embodiments in which the frame is a polygon. In embodiments in which the frame is circular or other non-polygon shape, the first opening 125 may extend along essentially an entirety of the top half of the frame or along a length defining the entirety of the length or width of the material to be carried by the frame. The frame may define the outer perimeter of the removable ornamentation 101. The frame may have a second opening 126, which is completed surrounded by the perimeter of the frame. The perimeter of the second opening 126 may be smaller than the perimeter of the removable ornamentation 101. The second opening 126 may be located on the surface of the removable ornamentation 101 opposing the side to which the second connector 111 is secured. The second opening may be adapted to display the decoration disposed on the material. The width of the removable ornamentation 101 between the outer perimeter of the removable ornamentation 101 and the perimeter of the second opening 126 may be adapted to secure and retain the material within the removable ornamentation 101.

In one embodiment, the ornamental scented frame clip 100 may be sold as a kit with a plurality of removable ornamentation 101 components and a single clip portion 104. In such an embodiment, multiple scent strips 103 may be included with the kit. In such an embodiment, each of the removable ornamentation 101 components within the kit may have a different aesthetic appearance. By way of example, and not as a limitation, the kit may be sold with a first removable ornamentation 101 having an appearance of a flower and a second removable ornamentation 101 having an appearance of a paw print. The first and second removable ornamentations 101 may be used interchangeably with a single clip portion 104 also contained in the kit.

The reservoir 114 may be fixedly secured to the second end of the first elongate member 105, which may also be the second end of the second angled portion 117. The reservoir 114 may extend outwardly across the outer side of the first elongate member 105. The reservoir 114 may have a cavity adapted to carry a scented substance. The scented substance may be a liquid, gel, or solid. In one embodiment, the scented substance may include cotton and fragrant oil. The fragrant oil may be absorbed and released by the cotton. In one embodiment, a pressed cotton cylinder, which may be referred to as a scent strip 103, may carry a fragrance and the scent strip 103 may be carried by the reservoir 114. The reservoir 114 may be adapted to carry liquid, gel, or other scented material, which may be absorbed and released by the scent strip 103.

The reservoir 114 may include a base 127, which may be elongate and have first and second side edges as well as front and back edges. A front side 128 may secure to the front edge of the base 127 and extend upwardly therefrom. A back side 129 may secure to the back edge of the base 127 and extend upwardly therefrom. A first side 130 may secure to the first side edge of the base 127 and extend upwardly therefrom, connecting the front side 128 to the back side 129. A second side 131 may secure to the second side edge of the base 127 and extend upwardly therefrom, connecting the front side 128 to the back side 129. The base, front side, back side, first side, and second side may define a cavity. Either the first side, second side, or both may have a slit or other opening through an entirety of the thickness of the side. In one embodiment, there may be a plurality of slits through an entirety of the thickness of the side. The one or more slits may be adapted to allow scent to escape from the cavity.

The cavity of the reservoir 114 may be covered by a scent strip cover 102. The scent strip cover 102 may be adapted to be captured and held in place by the reservoir 114 to cover or enclose the cavity. The scent strip cover 102 may slidably secure to the reservoir 114. The scent strip cover 102 may include an elongate member with a curvature matching the curvature of the top side of the reservoir 114. The scent strip cover 102 may have apertures located along its length to allow fragrance to escape from the scent strip 103 or other fragrant material carried by the scent strip reservoir 114. The scent strip cover 102 may have a handle portion extending beyond the scent strip reservoir 114. The handle portion may be adapted to allow a user to grasp the handle and remove the scent strip cover 102 from the scent strip reservoir 114 and gain access thereto for purposes of adding or removing fragrance, scent strips, or the like.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the description of the invention. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Thus the scope of the invention should be determined by the appended claims and their legal equivalents, and not by the examples given.

That which is claimed is:

1. An ornamental clip comprising:
a first elongate member having an inner side and an opposing outer side and further comprising:
 a first straight portion, having a first end and a second end, which opposes the first end, wherein the first end of the first straight portion connects directly to the first end of a transverse member, wherein the first straight portion extends downwardly from the transverse member and forms a right angle between the transverse member and the inner side of the first straight portion,
 a first angled portion having a first end and a second end, which opposes the first end, wherein the first end of the first angled portion connects directly to the second end of the first straight portion, wherein the first angled portion forms an obtuse angle between the first straight portion and the inner side of the first angled portion,
 a second straight portion having a first end and a second end, which opposes the first end, wherein the first end of the second straight portion connects directly to the second end of the first angled portion, wherein the second straight portion forms a reflex angle between the first angled portion and the inner side of the second straight portion, and
 a second angled portion having a first end and a second end, which opposes the first end, wherein the first end of the second angled portion connects directly to the second end of the second straight portion, wherein the second angled portion forms a reflex angle between the second straight portion and the inner side of the second angled portion;
a second elongate member having an outer side and an opposing inner side facing the inner side of the first elongate member;
the transverse member having a first end connected directly to a first end of the first elongate member and a second end connected directly to a first end of the second elongate member; and
a reservoir affixed to a second end of the first elongate member.

2. The ornamental clip of claim 1 wherein the first elongate member, the second elongate member, and the transverse member are cooperatively sized and positioned to form an interference fit with a picture frame positioned between the first and second elongate members.

3. The ornamental clip of claim 1 further comprising:
a first grip located on the inner side of the first elongate member; and
a second grip located on the inner side of the second elongate member and opposing the first grip;
wherein the first and second grip are configured to increase the coefficient of friction between the first or second elongate member and an item secured therebetween.

4. The ornamental clip of claim 1 further wherein the second elongate member further comprises:
a first angled portion connected directly to the transverse member at a first end of the first angled portion, wherein the first angled portion extends downwardly from the transverse member and forms an acute angle between the transverse member and the inner side of the second elongate member;
a straight portion having a first end connected directly to a second end of the first angled portion, which opposes the first end of the first angled portion, wherein the straight portion forms a reflex angle between the first angled portion and the inner side of the straight portion; and
a second angled portion having a first end connected directly to a second end of the straight portion, which opposes the first end of the straight portion, wherein the second angled portion forms a reflex angle between the second angled portion and the inner side of the straight portion.

5. The ornamental clip of claim 4 further comprising a grip located on the straight portion of the second elongate member and configured to increase the coefficient of friction between the second elongate member and an item secured between the first and second elongate members.

6. The ornamental clip of claim 1 further comprising:
a scented substance carried by the reservoir.

7. The ornamental clip of claim 1 further comprising:
ornamentation removably secured to the outer side of the first elongate member.

8. The ornamental clip of claim 7 wherein the ornamentation is adapted to carry a material having a thickness and a decoration disposed thereon and the ornamentation comprises:
a first opening adapted to receive the material and having a length greater than a width of the material; and
a second opening adapted to having a perimeter smaller than a perimeter of the material and adapted to display the decoration therethrough.

9. The ornamental clip of claim 7 further comprising:
a first connector secured to the outer side of the first elongate member; and
a second connector secured to an inner side of the ornamentation;
wherein the first and second connectors are cooperatively configured to secure to one another.

10. The ornamental clip of claim 1 further comprising a grip located on the second straight portion of the first elongate member and configured to increase the coefficient of friction between the first elongate member and an item secured between the first and second elongate members.

11. The ornamental clip of claim 1 wherein the reservoir connects directly to the second end of the second angled portion.

12. The ornamental clip of claim 1 further comprising:
ornamentation removably secured to the outer side of the first straight portion of the first elongate member.

13. The ornamental clip of claim 9 wherein the first connector comprises a mounting portion and the second connector comprises an opening adapted to receive and carry the mounting portion with an interference fit.

14. The ornamental clip of claim 1 wherein the reservoir comprises:

a base having a first side edge, a second side edge, which opposes the first side edge, a front edge, and a back edge;
a front side secured to the front edge and extending upwardly from the base;
a back side secured to the back edge and extending upwardly from the base;
a first side secured to the first side edge, the front side, and the back side and extending upwardly from the base; and
a second side secured to the second side edge, the front side, and the back side and extending upwardly from the base; and
wherein the base, front side, back side, first side, and second side define a cavity.

15. The ornamental clip of claim 14 wherein the first side comprises a plurality of openings through an entirety of a thickness of the first side; and
wherein the second side comprises a plurality of openings through an entirety of a thickness of the second side.

16. The ornamental clip of claim 14 further comprising:
a cover carried by the reservoir and cooperatively formed with the reservoir to enclose the cavity.

17. An ornamental clip comprising:
a first elongate member having an inner side and an opposing outer side
a first straight portion, having a first end and a second end, which opposes the first end, wherein the first end of the first straight portion connects directly to the first end of a transverse member, wherein the first straight portion extends downwardly from the transverse member and forms a right angle between the transverse member and the inner side of the first straight portion,
a first angled portion having a first end and a second end, which opposes the first end, wherein the first end of the first angled portion connects directly to the second end of the first straight portion, wherein the first angled portion forms an obtuse angle between the first straight portion and the inner side of the first angled portion,
a second straight portion having a first end and a second end, which opposes the first end, wherein the first end of the second straight portion connects directly to the second end of the first angled portion, wherein the second straight portion forms a reflex angle between the first angled portion and the inner side of the second straight portion, and
a second angled portion having a first end and a second end, which opposes the first end, wherein the first end of the second angled portion connects directly to the second end of the second straight portion, wherein the second angled portion forms a reflex angle between the second straight portion and the inner side of the second angled portion;
a second elongate member having an outer side and an opposing inner side facing the inner side of the first elongate member;
the transverse member having a first end connected directly to a first end of the first elongate member and a second end connected directly to a first end of the second elongate member; and
a reservoir affixed to a second end of the first elongate member;
a scented substance carried by the reservoir; and
ornamentation removably secured to the outer side of the first elongate member; and
wherein the first elongate member, the second elongate member, and the transverse member are cooperatively sized and positioned to form an interference fit with a picture frame positioned between the first and second elongate members.

18. The ornamental clip of claim 17 wherein the ornamentation is adapted to carry a material having a thickness and a decoration disposed thereon and the ornamentation comprises:
a first opening adapted to receive the material and having a length greater than a width of the material; and
a second opening adapted to having a perimeter smaller than a perimeter of the material and adapted to display the decoration therethrough.

19. An ornamental clip comprising:
a first elongate member having an inner side and an opposing outer side and comprising:
a first straight portion, having a first end and a second end, which opposes the first end, wherein the first end of the first straight portion connects directly to the first end of the transverse member, wherein the first straight portion extends downwardly from the transverse member and forms a right angle between the transverse member and the inner side of the first straight portion,
a first angled portion having a first end and a second end, which opposes the first end, wherein the first end of the first angled portion connects directly to the second end of the first straight portion, wherein the first angled portion forms an obtuse angle between the first straight portion and the inner side of the first angled portion,
a second straight portion having a first end and a second end, which opposes the first end, wherein the first end of the second straight portion connects directly to the second end of the first angled portion, wherein the second straight portion forms a reflex angle between the first angled portion and the inner side of the second straight portion,
a second angled portion having a first end and a second end, which opposes the first end, wherein the first end of the second angled portion connects directly to the second end of the second straight portion, wherein the second angled portion forms a reflex angle between the second straight portion and the inner side of the second angled portion, and
a first grip located on the second straight portion;
a second elongate member having an outer side and an opposing inner side facing the inner side of the first elongate member and comprising:
a first angled portion connected directly to the transverse member at a first end of the first angled portion, wherein the first angled portion extends downwardly from the transverse member and forms an acute angle between the transverse member and the inner side of the second elongate member,
a straight portion having a first end connected directly to a second end of the first angled portion, which opposes the first end of the first angled portion, wherein the straight portion forms a reflex angle between the first angled portion and the inner side of the straight portion,
a second angled portion having a first end connected directly to a second end of the straight portion, which opposes the first end of the straight portion, wherein the second angled portion forms a reflex angle between the second angled portion and the inner side of the straight portion, and a second grip located on the inner side of the straight portion and cooperatively configured with the first grip of the first elongate member to increase the coefficient of friction between the first and second elongate members and an item secured between the first and second elongate members;

a transverse member having a first end connected directly to a first end of the first elongate member and a second end connected directly to a first end of the second elongate member;

a reservoir affixed to the second end of the second angled portion of the first elongate member and defining a cavity;

a cover carried by the reservoir and cooperatively formed with the reservoir to enclose the cavity;

ornamentation removably secured to the outer side of the first straight portion of the first elongate member and adapted to carry a material having a thickness and a decoration disposed thereon, wherein the ornamentation comprises:

a first opening adapted to receive the material and having a length greater than a width of the material, and a second opening adapted to having a perimeter smaller than a perimeter of the material and adapted to display the decoration therethrough;

a first connector secured to the outer side of the first elongate member;

a second connector secured to an inner side of the ornamentation and cooperatively configured to secure to the first connector; and a scented substance carried by the reservoir;

wherein the first elongate member, the second elongate member, and the transverse member are cooperatively sized and positioned to form an interference fit with a picture frame positioned between the first and second elongate members; and wherein the first and second grip are configured to increase the coefficient of friction between the first or second elongate member and an item secured therebetween.

* * * * *